US00PP35516P2

(12) United States Plant Patent
Bell

(10) Patent No.: US PP35,516 P2
(45) Date of Patent: Dec. 5, 2023

(54) BLUEBERRY PLANT NAMED 'RIDLEY 2503'

(50) Latin Name: ***Vaccinium* hybrid**
Varietal Denomination: Ridley 2503

(71) Applicant: MOUNTAIN BLUE ORCHARDS PTY LTD, Lindendale (AU)

(72) Inventor: Ridley Bell, Lindendale (AU)

(73) Assignee: Mountain Blue Orchards PTY LTD, Lindendale (AU)

( * ) Notice: Subject to any disclaimer, the term of this patent is extended or adjusted under 35 U.S.C. 154(b) by 0 days.

(21) Appl. No.: 17/803,960

(22) Filed: Feb. 7, 2023

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

| | | | |
|---|---|---|---|
| PP22,778 | P3 | 6/2012 | Wright et al. |
| PP25,432 | P3 | 4/2015 | Bell |
| PP29,470 | P3 | 7/2018 | Bell |

*Primary Examiner* — Keith O. Robinson
(74) *Attorney, Agent, or Firm* — Plant & Planet Law Firm

(57) ABSTRACT

The new blueberry plant variety 'Ridley 2503' is provided. 'Ridley 2503' is a commercial variety intended for use as fresh fruit for shipping, hand pick, customer pick, machine harvest and processing markets and as a home garden plant. The variety is produced from a cross of 'Ridley 4408' (U.S. Plant Pat. No. 29,470) and 'Ridley1403' (U.S. Plant Pat. No. 25,432), which can be distinguished by its outstanding features.

6 Drawing Sheets

Latin name of the genus and species:
Genus—*Vaccinium.*
Species—hybrid.
Variety denomination: The new blueberry plant claimed is of the variety denominated 'Ridley 2503'.

BACKGROUND OF THE INVENTION

The present invention relates to a new and distinct perennial variety of *Vaccinium* hybrid (Southern Highbush Blueberry), which has been given the variety denomination of 'Ridley 2503'. Its market class is that of a fruiting plant. 'Ridley 2503' is intended for use as fresh fruit for shipping, customer pick and processing markets and as a home garden plant.

The new *Vaccinium* hybrid cultivar is a selection resulting from seedlings produced in a breeding program of *Vaccinium* at Lindendale, NSW, Australia in 2013 from the controlled pollination of seed parent 'Ridley 4408' (U.S. Plant Pat. No. 29,470) with pollen parent 'Ridley 1403' (U.S. Plant Pat. No. 25,432). The seed parent was produced from a seedling selection of 'S01-15-01' (unpatented) and 'C00-09' (U.S. Plant Pat. No. 22,778). The pollen parent was produced from a seedling selection of 'S02-25-05' (not patented) and pollen parent 'S03-08-02' (not patented).

The new cultivar was discovered and selected as a single plant within a population of 100 resulting *Vaccinium* hybrid plants from this controlled pollination in 2016 in a commercial field plantation environment at Tabulam, New South Wales, Australia.

The new blueberry cultivar was designated 'M16-25-03' and has been planted in replicated trials since 2017 at the commercial farms at Tabulam, New South Wales, Australia.

Asexual reproduction of the new cultivar by cutting propagation since 2016 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The following are the most outstanding and distinguishing characteristics of the new cultivar when grown under normal horticultural practices in Tabulam, New South Wales, Australia and have been repeatedly observed and can be used to distinguish 'M16-25-03' ('Ridley 2503') as a new and distinct cultivar of *Vaccinium* hybrid plant:

1. aromatic flavor profile;
2. very large to jumbo fruit size;
3. firm/crisp texture;
4. high yield;
5. mid season flower and fruit timing; and
6. moderately loose fruit clusters that are easy to pick and suited to machine harvest.

BRIEF DESCRIPTION OF THE DRAWINGS

The accompanying photographic illustration shows typical specimens in full color of the foliage and fruit of the new variety 'Ridley 2503.' The colors are as true as is reasonably possible in a color representation of this type.

The colors in the photographs are as close as possible with the photographic and printing technology utilized. The color values cited in the detailed botanical description accurately describe the colors of the new blueberry.

DETAILED BOTANICAL DESCRIPTION

Figure 1:
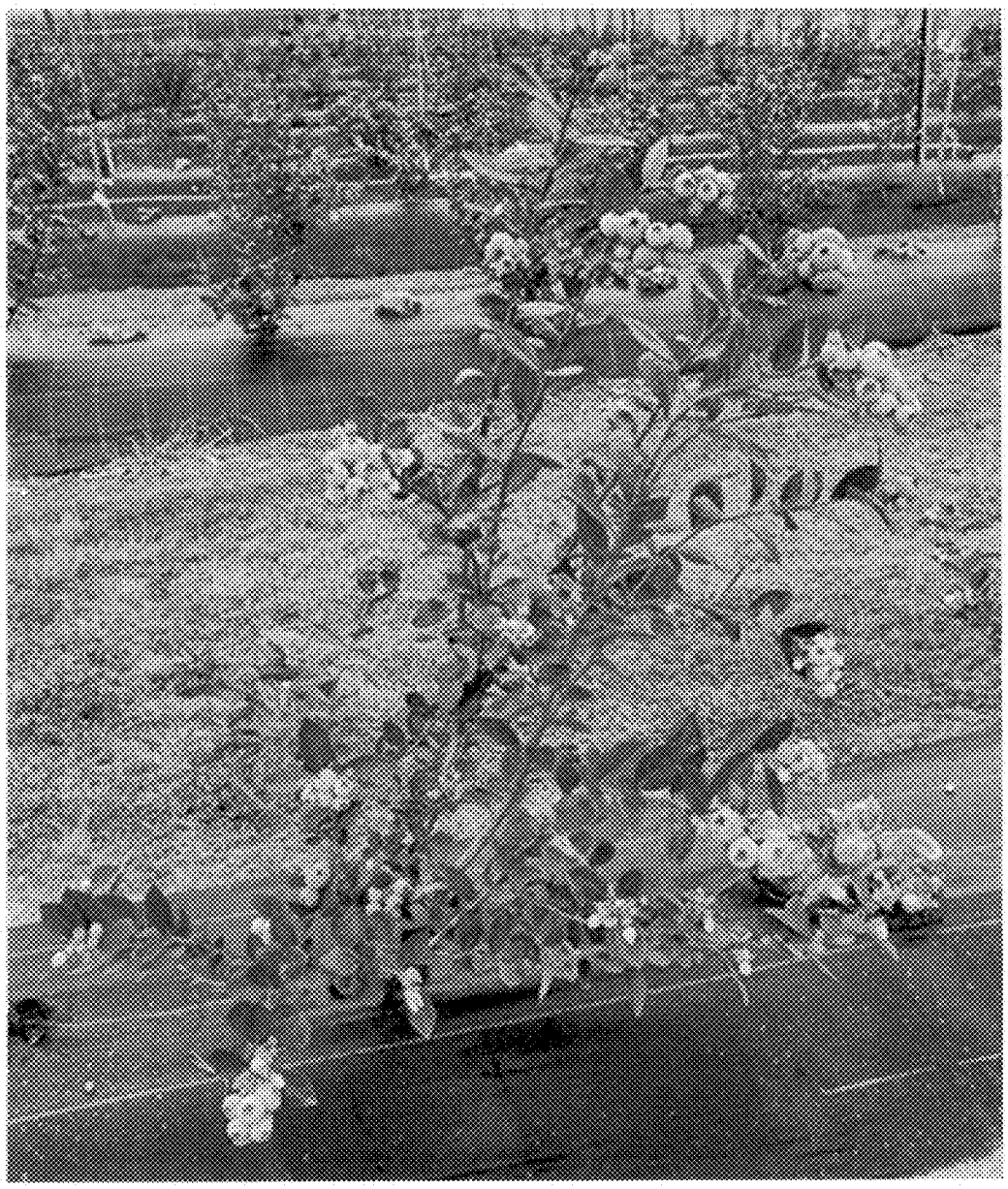
FIG. 1 is a photograph of the new variety 'Ridley 2503' showing the plant's upright/whippy growth habit at approximately 1 year of age.
Figure 2:
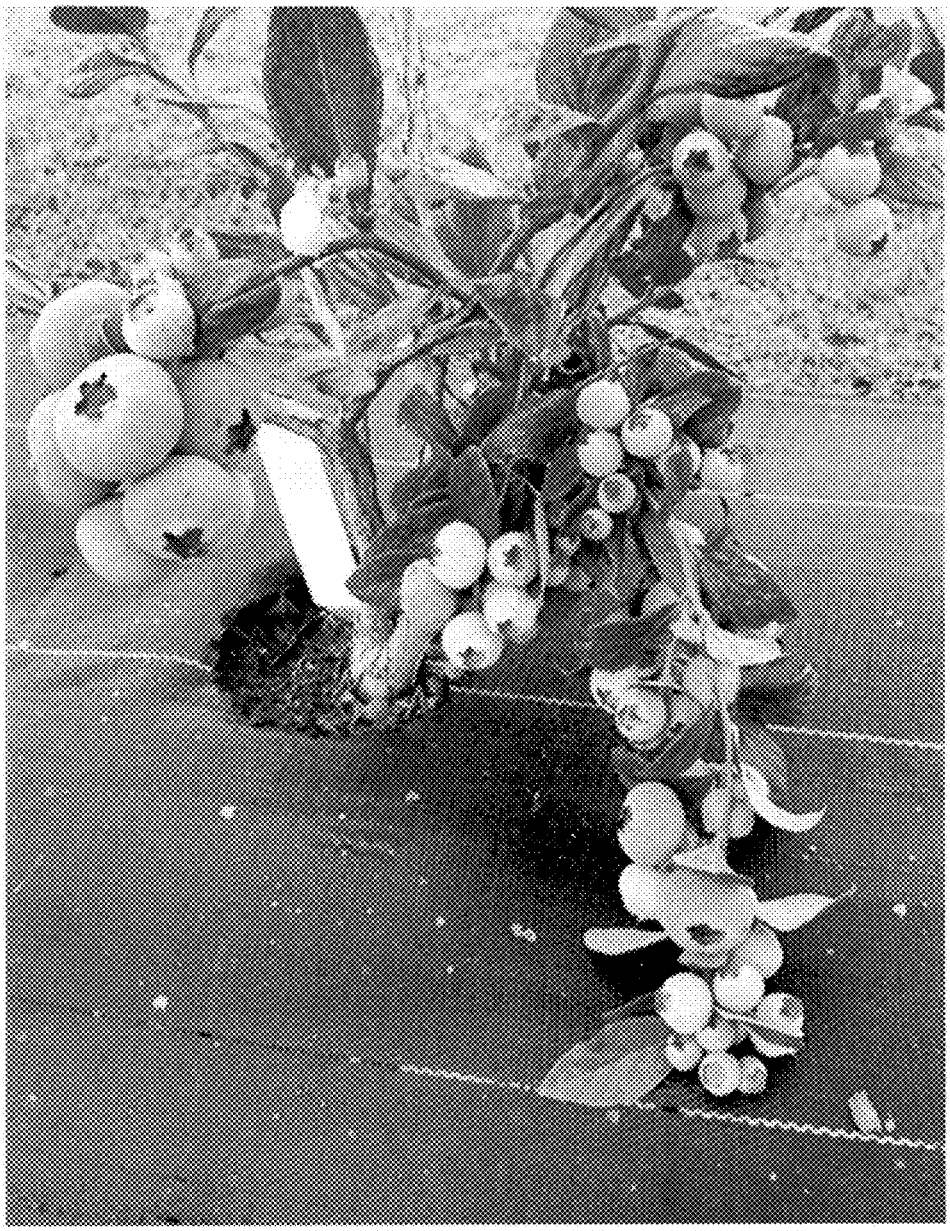
FIG. 2 is a photograph of the cluster of the fruit of 'Ridley 2503' at approximately 1 year of age.
Figure 3:
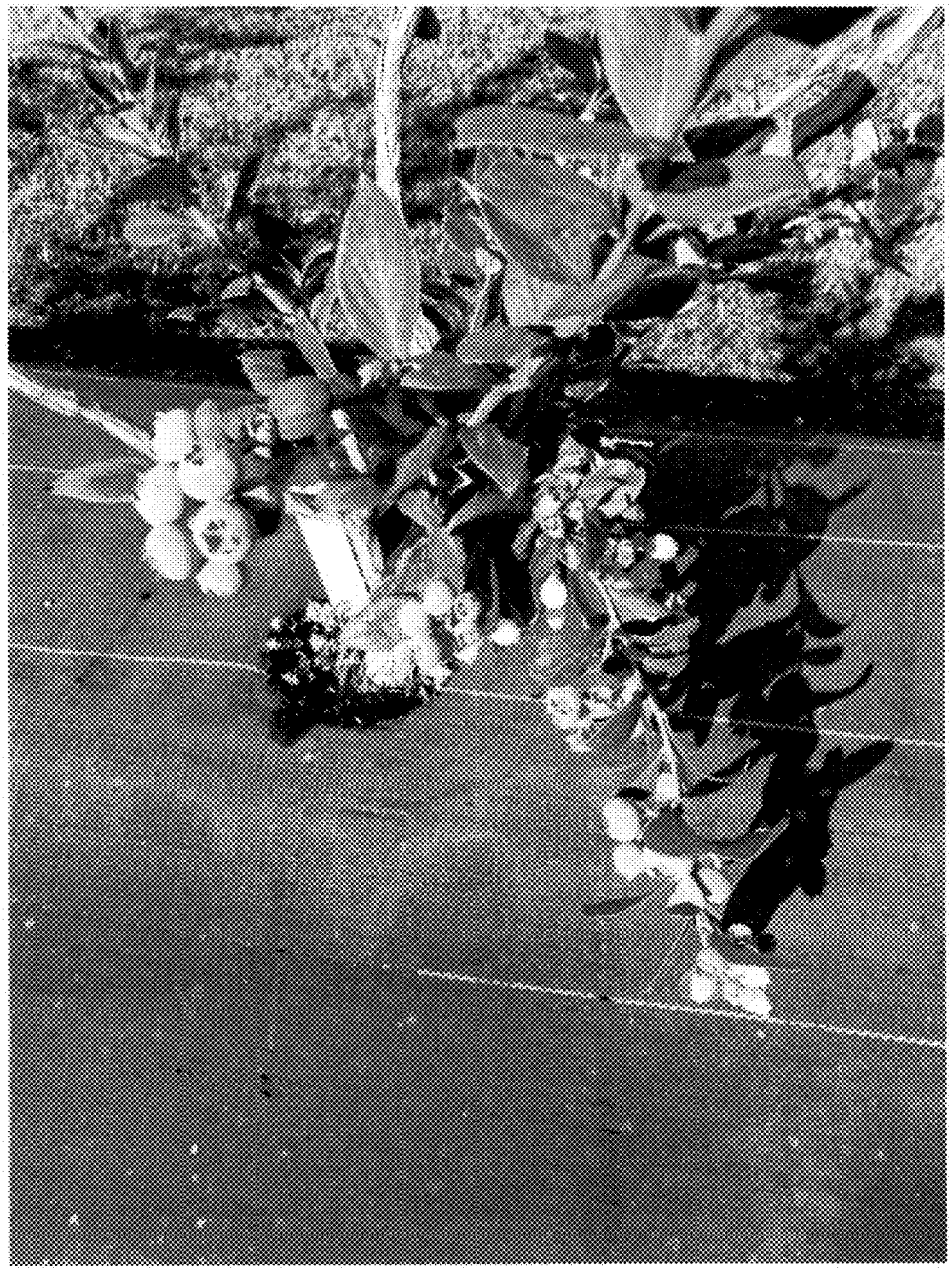
FIG. 3 is a photograph of the flowers and immature fruit of 'Ridley 2503' at approximately 1 year of age.
Figure 4:
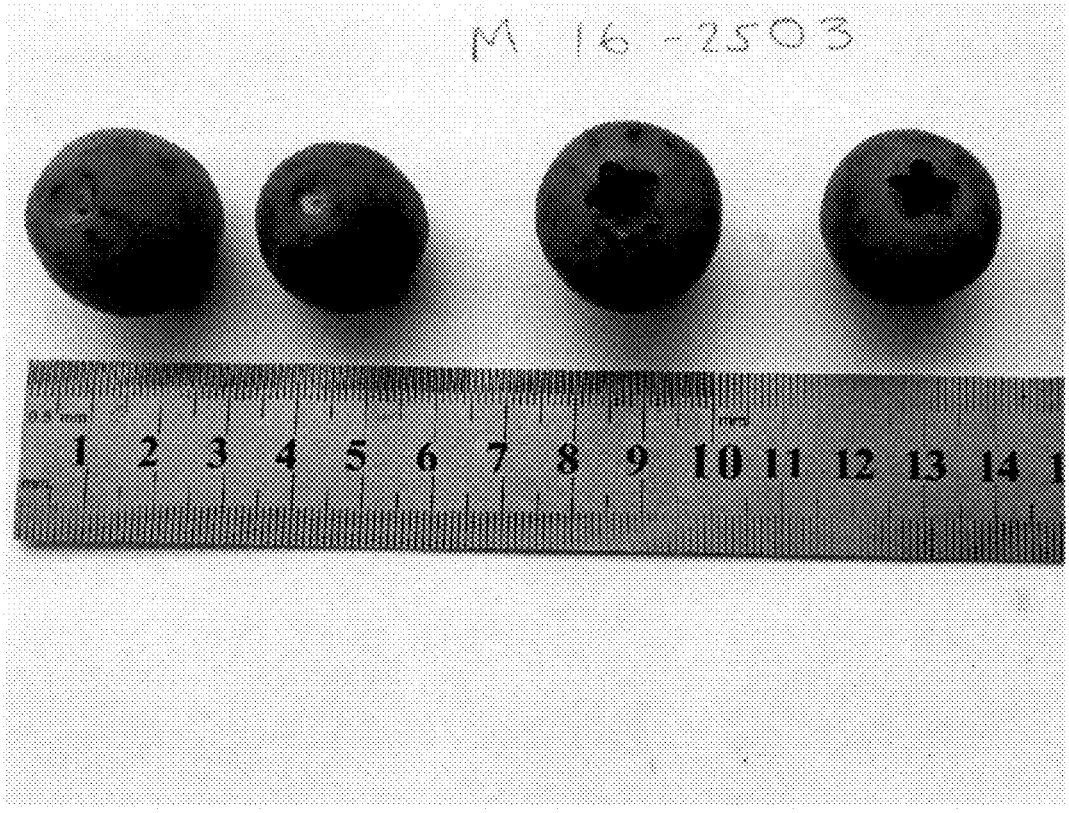
FIG. 4 is a photograph of the fruit of 'Ridley 2503'.
Figure 5:
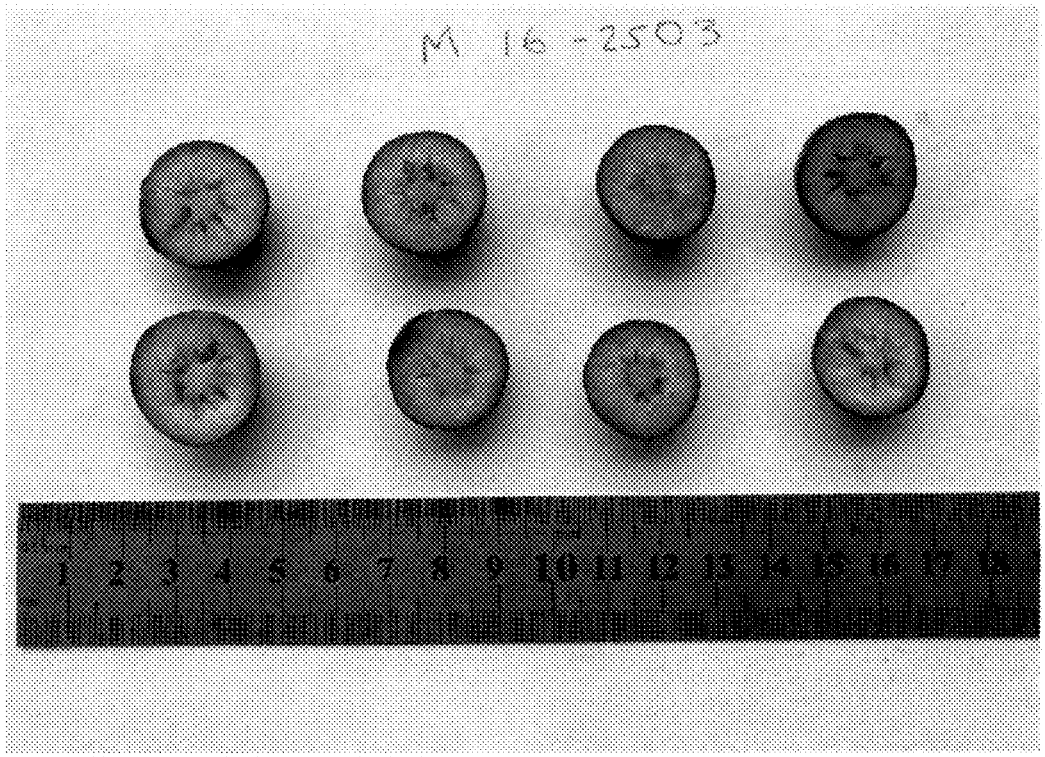
FIG. 5 is a photograph of the cross section of the fruit of 'Ridley 2503'.
Figure 6:
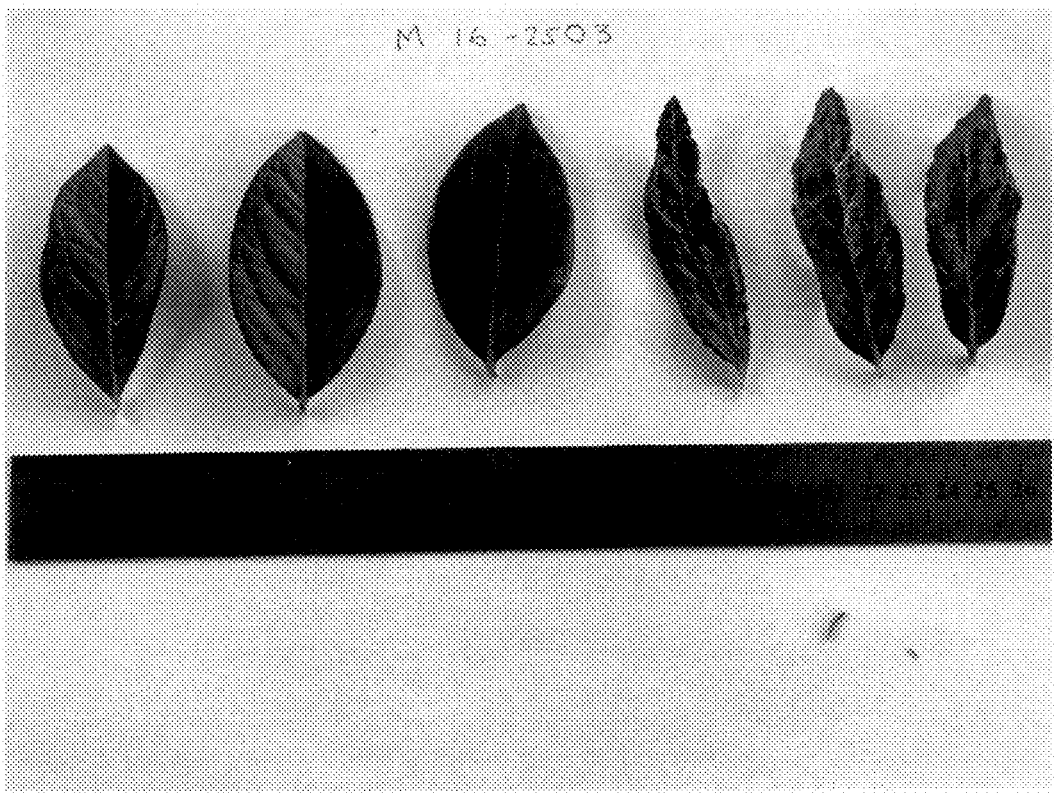
FIG. 6 is a photograph of the leaves of 'Ridley 2503' showing the typical leaf and the variegated variant that is a stable and uniform leaf variation through multiple cycles of reproduction.

The following detailed description sets forth the distinctive characteristics of 'Ridley 2503'. The data which define these characteristics were collected from asexual reproductions of the original selection. Dimensions, sizes, colors, and other characteristics are approximations and averages set forth as accurately as possible. Foliage measurements were taken using the typical leaf. The plant history was taken on plants approximately 1-3 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia. Color notations are based on *The Royal Horticultural Society Colour Chart*, of The Royal Horticultural Society, London, sixth edition.

Classification:

*a. Family.*—Ericaceae.
*b. Genus.*—*Vaccinium.*
*c. Species.*—hybrid.
*d. Common name.*—Southern Highbush Blueberry.

Parentage: Female Parent—'Ridley 4408' (U.S. Plant Pat. No. 29,470). Male Parent—'Ridley1403' (U.S. Plant Pat. No. 25,432).

Market class: A fruiting plant intended for use as fresh fruit for shipping, hand pick, customer pick, machine harvest and processing markets and as a home garden plant.

PLANT

General:

*Parentage.*—Female Parent — 'Ridley 4408' (U.S. Plant Pat. No. 29,470). Male Parent — 'Ridley1403' (U.S. Plant Pat. No. 25,432).
*Plant height.*—Average 1.4 m.
*Plant width.*—Average 1.2 m.
*Growth habit.*—Semi-upright/whippy.
*Growth.*—Medium-strong.
*Productivity.*—3.4 kg per plant in $2^{nd}$ harvest.
*Cold hardiness.*—Has not been tested/expected to be low.
*Cold tolerance.*—Has not been tested/expected to be low.
*Chilling requirement.*—Has not been tested/expected to be low.
*Tolerance to disease.*—Hasn't been tested.
*Leafing.*—Vegetative bud burst is medium — high.
*Twigginess.*—Moderate.
*Vigor.*—Strong.

STEM

General:

*Suckering tendency.*—Average, 4-5 canes/plant.
*Mature cane color.*—197B/199D.
*Mature cane length.*—60-90 cm. Average 72 cm.
*Mature cane width.*—Average 24 mm.
*Bark texture.*—Rough.
*Surface texture of new wood.*—Smooth-medium.
*Internode length on strong, new shoots.*—Average 19.07 mm.
*Fruiting wood.*—Average length 68.8 mm.
*One year old shoot color.*—Reddish green at time of flowering/fruiting. Top 144B, underside 183B.

FOLIAGE

General:

*Time of beginning of leaf bud burst.*—Mid (from week 38 at Tabulam, NSW, Australia).
*Leaf color (top side).*—137A/143A.
*Leaf color (under side).*—138B/139D.
*Leaf arrangement.*—Alternate.
*Leaf shape.*—Elliptic.
*Leaf margins.*—Entire.
*Undulation of margin.*—Weak.
*Leaf venation.*—Reticulate.
*Leaf apices.*—Acute.
*Leaf bases.*—Acute.
*Leaf length.*—Average 65 mm.
*Leaf width.*—Average 36 mm.
*Leaf length/width ratio.*—1.8:1.
*Leaf nectaries.*—Absent.
*Pubescence of upper side.*—Absent.
*Pubescence of lower side.*—Absent.
*Cross sectional profile.*—Flat/straight.
*Longitudinal profile.*—Flat/Straight.
*Attitude.*—Upright/Semi-upright.

Petioles:

*Length.*—Average 3.8 mm.
*Width.*—Average 2.1 mm.
*Color.*—142C/145B.

FLOWERS

General:

*Time of beginning of flowering.*—Mid (week 19 at Tabulam, NSW Australia).
*Time of 50% anthesis.*—Week 24-26 at Tabulam, NSW Australia.
*Flower shape.*—Urceolate.
*Flower bud density.*—Moderate.
*Flower fragrance.*—Weak. A very mild sweet smell.

Corolla:

*Color.*—White 155C.
*Length.*—Average 11.4 mm.
*Width.*—Average 9 mm.
*Aperture width.*—Average 3.6 mm.
*Anthocyanin coloration of corolla.*—Absent to weak.
*Corolla ridges.*—Present.
*Protrusion of stigma.*—Nil.

Inflorescence:

*Length.*—Average 46.8 mm.
*Diameter.*—Average 34.7 mm.

*Length of peduncle*.—Average 38.4 mm.
*Surface texture of peduncle*.—Smooth.
*Color of peduncle*.—Light green 144D/144C.
*Length of pedicel*.—Average 7.7 mm.
*Surface texture of pedicel*.—Smooth.
*Color of pedicel*.—Light green 144D/144C.
*Number of flowers per cluster*.—Average 7.
*Flower cluster density*.—Moderate.

Calyx (with sepals):
*Diameter*.—7.5 mm.
*Color* (*sepals*).—143C.

Stamen:
*Length*.—7 mm.
*Number per flower*.—8-11.
*Filament color*.—142D.

Pistil:
*Length*.—12 mm.
*Style length*.—10 mm.
*Ovary color* (*exterior*).—144A/146A.

Anther:
*Length*.—4 mm.
*Number*.—8-11.
*Color*.—163A/N167A.

Pollen:
*Abundance*.—Medium-high.
*Color*.—158C.
*Self-compatibility*.—100%.

FRUIT

General:
*Time of fruit ripening*.—Mid season (from week 30 at Tabulam, NSW, Australia).
*Time of* 50% *maturity*.—Week 40 at Tabulam, NSW, Australia.
*Fruit development period*.—6-8 weeks.
*Fruit bloom intensity*.—Medium to strong.
*Fruiting type*.—On one year old shoots only.
*Cluster density*.—Moderate to loose.
*Unripe fruit color*.—142A.
*Ripe berry color*.—202A.
*Berry surface wax abundance*.—Moderate to strong.
*Berry flesh color*.—145C.
*Berry weight*.—4.6 g.
*Berry height from calyx to scar*.—17 mm.
*Berry diameter*.—23 mm.
*Berry shape*.—Oblate.
*Fruit stem scar*.—Large.
*Sweetness when ripe*.—High (15° Bx).
*Firmness when ripe*.—Moderate to high (62% Durofel).
*Acidity when ripe*.—Low to moderate.
*Storage quality*.—Not assessed.
*Suitability for mechanical harvesting*.—Very suitable.
*Self-fruitfulness*.—100%.
*Uses*.—Fresh fruit for shipping, customer pick and processing markets and as a home garden plant.

SEED

General:
*Seed abundance in fruit*.—Not assessed.
*Seed color*.—Not assessed.
*Seed dry weight*.—Not assessed.
*Seed length*.—Not assessed.

COMPARISON BETWEEN PARENTAL AND COMMERCIAL CULTIVARS

TABLE 1

| Organ | Context | 'Ridley 2503' | 'Ridley 4408' (U.S. Plant Pat. 29,470) | 'Ridley 1403' (U.S. Plant Pat. 25,432) | Ridley 1702 (U.S. Plant Pat. 33,717) |
|---|---|---|---|---|---|
| Plant | Vigor | Strong | Medium | Strong | Strong |
| Plant | Growth habit | Upright/ whippy | Upright to semi-upright | Upright to semi-upright | Upright/ whippy |
| One-year-old shoot | Color | Green | Green | Green | Green |
| One-year-old shoot | Length of internode | Medium | Medium | Medium | Medium |
| Leaf | Length | Long | Long | Long to very long | Long |
| Leaf | Width | Broad | Broad | Broad | Broad |
| Leaf | Shape | Elliptic | Elliptic | Elliptic | Elliptic |
| Leaf | Color of upper side | Green | Green | Green | Green |
| Leaf | Intensity of green color on upper side (varieties with green leaf color only) | Medium | Medium | Medium | Medium |
| Leaf | Margin | Entire | Entire | Entire | Entire |
| Flower bud | Anthocyanin coloration | Weak | Weak | Weak | Weak |
| Flower | Shape of corolla | Urceolate | Urceolate | Urceolate | Urceolate |
| Flower | Size of corolla tube | Medium | Medium | Medium to large | Medium |

TABLE 1-continued

| Organ | Context | 'Ridley 2503' | 'Ridley 4408' (U.S. Plant Pat. 29,470) | 'Ridley 1403' (U.S. Plant Pat. 25,432) | Ridley 1702 (U.S. Plant Pat. 33,717) |
|---|---|---|---|---|---|
| Flower | Anthocyanin coloration of corolla tube | Absent or very weak | Absent or very weak | Absent or very weak | Absent or very weak |
| Flower | Ridges on corolla tube | Present | Present | Present | Present |
| Fruit cluster | Density | Medium to loose | Medium to dense | Medium to dense | Medium to loose |
| Unripe fruit | Intensity of green color | Light | Light | Light | Light |
| Fruit | Size | Very large | Medium | Very large | Very large |
| Fruit | Shape in longitudinal section | Oblate | Round | Round | Oblate |
| Fruit | Attitude of sepals | Incurving | Erect | Erect | Erect |
| Fruit | Diameter of calyx basin | Large | Large | Large | Large |
| Fruit | Depth of calyx basin | Deep | Deep | Deep | Deep |
| Fruit | Intensity of bloom | Medium strong | Strong | Medium | Medium to strong |
| Fruit | Color of skin | Dark blue | Dark blue | Dark blue | Dark blue |
| Fruit | Firmness | Firm | Firm | Very firm | Very firm |
| Fruit | Sweetness | High | High | High | Medium to high |
| Fruit | Acidity | Low to medium | High | Low | Low to medium |
| Time of | Vegetative bud burst | Medium | Early to medium | Early to medium | Medium |
| Time of | Beginning of flowering | Medium | Early to medium | Early to medium | Medium |
| Time of | Beginning of fruit ripening | Medium | Early to medium | Early to medium | Medium |

The invention claimed is:

1. A new and distinct variety of blueberry plant named 'Ridley 2503', substantially as illustrated and described herein.

* * * * *